United States Patent [19]

Chopin

[11] Patent Number: 5,133,717
[45] Date of Patent: Jul. 28, 1992

[54] SACRAL SUPPORT SADDLE FOR A SPINAL OSTEOSYNTHESIS DEVICE

[75] Inventor: Daniel Chopin, le Touquet Paris Plage, France

[73] Assignee: Societe de Fabrication de Material Orthopedique Sofamor, Paris, France

[21] Appl. No.: 651,624

[22] Filed: Feb. 7, 1991

[30] Foreign Application Priority Data

Feb. 8, 1990 [FR] France .................. 90 01474

[51] Int. Cl.⁵ .................................................. A61F 5/00
[52] U.S. Cl. ........................................ 606/61; 606/59; 606/73
[58] Field of Search ................ 128/69; 606/60, 61, 606/73, 53, 72

[56] References Cited

U.S. PATENT DOCUMENTS

| | | |
|---|---|---|
| 3,741,205 | 6/1973 | Markolf et al. |
| 4,648,388 | 3/1987 | Steffee ............... 606/73 X |
| 4,719,905 | 1/1988 | Steffee ............... 606/61 X |
| 4,771,767 | 9/1988 | Steffee ............... 606/61 X |
| 4,946,458 | 8/1990 | Harms et al. ......... 606/61 |
| 5,000,166 | 3/1991 | Karpf ................ 606/61 X |
| 5,005,562 | 4/1991 | Cortel ............... 606/59 X |

FOREIGN PATENT DOCUMENTS

| | | | |
|---|---|---|---|
| 0299160 | 1/1989 | European Pat. Off. | ......... 606/60 |
| 0348272 | 6/1989 | European Pat. Off. | ......... 606/61 |
| 2178323 | 2/1987 | United Kingdom . | |

Primary Examiner—Robert A. Hafer
Assistant Examiner—Brian E. Hanlon
Attorney, Agent, or Firm—Wenderoth, Lind & Ponack

[57] ABSTRACT

A sacral support saddle has an eye (36) for receiving a first screw (38) and a cylindrical hole (37) with an axis (X5) of inclination such that, when the saddle (29) is positioned on the sacrum, the screw (38) is inserted into the sacral plate and towards the upper axis of the latter. A U-shaped body (32) delimits a channel (34) for receiving a rod, and a stopper (7) locks the rod (8) in this body. A hole (33) for passage of a second screw (42) has an axis (Y5) divergent relative to the axis (X5) of the hole of the eye in such a way as to be oriented towards the iliac mass when the saddle is positioned on the sacrum. This saddle and its two screws (38, 42) provide for a reliable anchoring of the rod of the device to the sacrum by virtue of the penetration of the screws into solid regions of the latter. This, in practice, avoids any risk of pulling out and, consequently, a second surgical intervention.

12 Claims, 3 Drawing Sheets

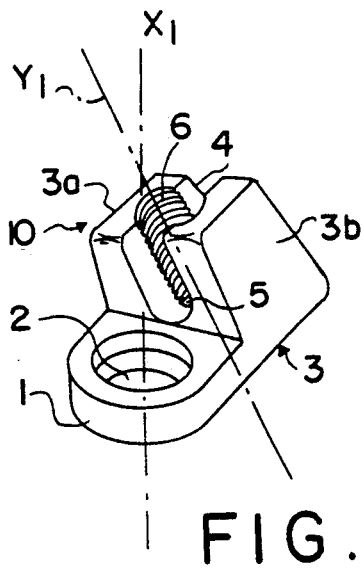
FIG. 1
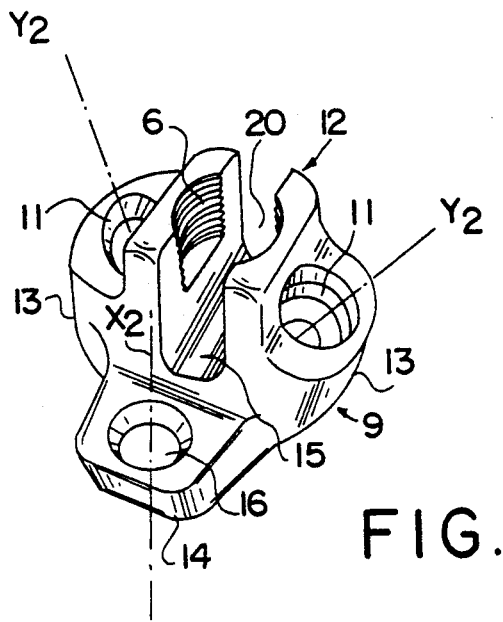
FIG. 2
FIG. 3
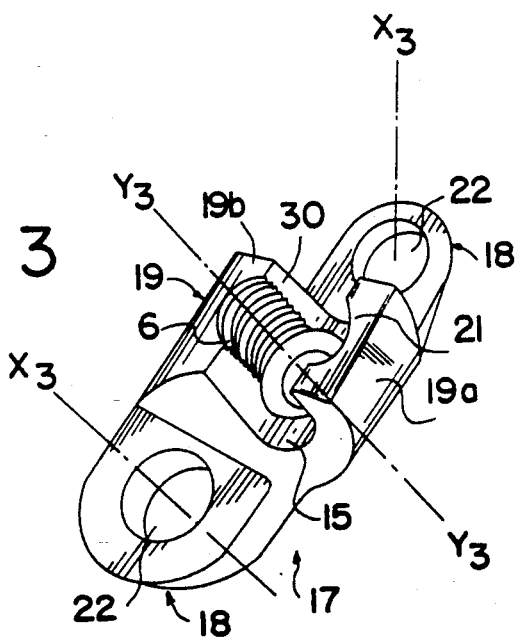
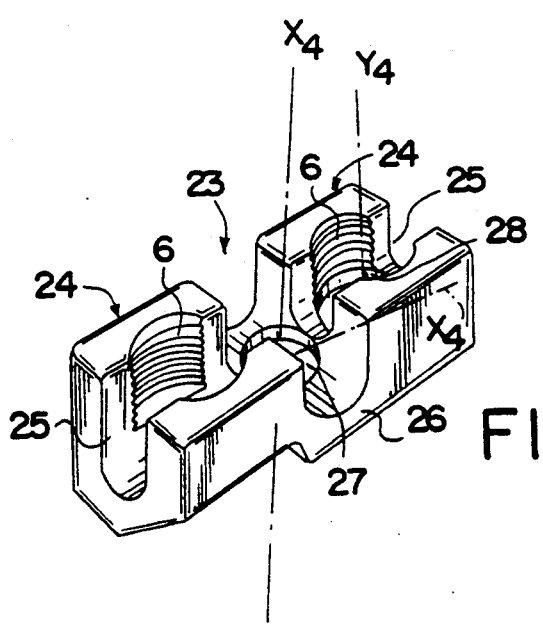
FIG. 4

SACRAL SUPPORT SADDLE FOR A SPINAL OSTEOSYNTHESIS DEVICE

BACKGROUND OF THE INVENTION

The present invention relates to a sacral support saddle for a spinal osteosynthesis device.

It is known that obtaining a firm sacral support in spinal osteosynthesis remains a problem which has not as yet been solved. The bone of the sacrum is, in fact, for the most part spongy and porous, especially in older subjects, and therefore has a low strength. To date, use has been made of a single screw positioned at S1 (first vertebra of the sacrum), in which the lower end of the rod of the corresponding device is inserted, the other screws being driven into the two lumbar vertebrae adjacent to the sacrum. However, the low strength of the sacrum and the considerable leverage arm exerted on the screw develop stresses which result in risks of pulling out the screw.

When such a pulling out takes place, it is then necessary for the surgeon to conduct a second intervention, generally involving the positioning of a second screw at S2 (second vertebra of the sacrum). The device thus becomes bulky. Moreover, this second surgical intervention can entail neurological risks on account of the presence of nerves at S2, and it is more substantial than the preceding intervention and is psychologically poorly received by the patient.

SUMMARY OF THE INVENTION

The aim of the invention is therefore to propose a satisfactory solution to this problem, providing for a sufficiently firm and reliable sacral support so as to avoid the need for a second intervention.

According to the invention, the sacral support saddle comprises:

at least one eye for receiving a first screw, and having a cylindrical hole with an axis of inclination such that, when the saddle is positioned on the sacrum, the screw is inserted into the sacral plate and towards the upper axis of the latter, at least one U-shaped body delimiting a channel for receiving a rod of the device, and a means for locking the rod in this U-shaped body, at least one hole for passage of a second screw, whose axis is divergent relative to the axis of the hole of the eye, in such a way as to be oriented towards an iliac mass when the saddle is positioned on the sacrum.

Thus, the first screw is driven into a region of the sacrum which is stronger than that which received the screws used hitherto, by virtue of its suitable inclination. The same applies to the second screw which diverges from the first screw and is anchored in the iliac mass.

The insertion of the screws in divergent directions and in the strongest zones of the sacrum thus considerably improves the anchoring, and this ordinarily eliminates any risk of pulling out of the screws and of the saddle.

According to a first embodiment of the invention, the hole for passage of the second screw is made in the base of the U-shaped body.

According to a second embodiment, the hole for passage of the second screw is made in a lateral projection of the U-shaped body, and the axis of this hole is inclined by a suitable angle to a median plane of the channel of the body, passing through the base of the latter, the eye being arranged essentially in the extension of the base of the channel.

The inclination of the axis of the hole of the eye to the median plane is preferably of the order of about 20 to 30 degrees.

The saddle according to the invention and its screws can be used for all sacral fixations, lumbosacral instruments, adult lumbar scolioses necessitating fixation up to the sacrum, paralytic scolioses and spondylolisthesis.

BRIEF DESCRIPTION OF THE DRAWINGS

Other characteristics and advantages of the invention will emerge in the course of the description which follows, and in which reference is made to the attached drawings, which illustrate several embodiments, given by way of non-limiting examples, wherein:

FIG. 1 is a perspective view of a first embodiment of the saddle according to the invention, without its screws;

FIGS. 2 to 4 are perspective views, similar to FIG. 1, of three other embodiments of the saddle according to the invention, without their screws;

DETAILED DESCRIPTION OF THE PREFERRED EMBODIMENTS

Figure 6:
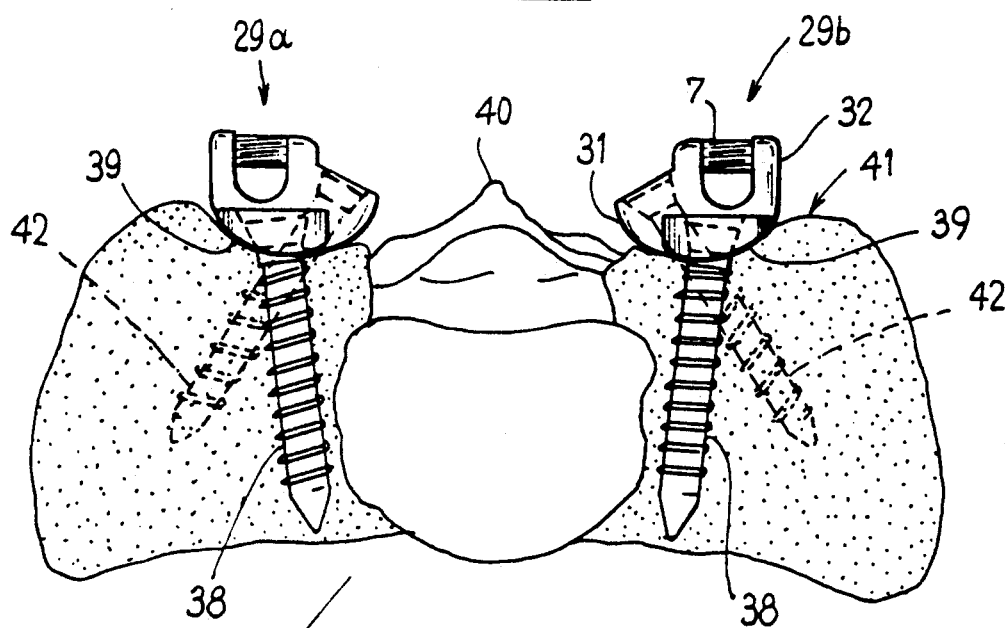
FIG. 6 is an elevation view of a sacrum, seen from the fifth lumbar vertebra, this sacrum being provided with two saddles according to the embodiment in FIG. 5 and equipped with their screws.

The saddle 10 shown in FIG. 1 is intended for sacral support in a spinal osteosynthesis device. It comprises an eye 1 for receiving a first screw (not shown), in which eye there is made a cylindrical hole 2 with an axis X1 of inclination such that, when the saddle 10 is positioned on the sacrum, the corresponding screw passing through the hole 2 is inserted in the sacral plate and towards the upper axis of the latter. A U-shaped body 3, made one-piece with the eye 1, delimits a channel 4 for receiving a rod (not shown) of the device. A hole 5 for passage of a second screw (not shown) is made in the base of the body 3, whose axis Y1 is divergent relative to the axis X1, in such a way as to be oriented towards the iliac mass when the saddle is positioned on the sacrum.

The angle between the two axes X1 and Y1 can vary considerably.

On the inside walls of the channel 4 there are tapped sections 6 able to receive a corresponding threaded plug, such as 7 (FIGS. 5 and 6), for locking a rod 8 (FIG. 7) inserted in the channel 4.

In a second embodiment, a saddle 9, illustrated in FIG. 2, comprises two holes 11 for passage of the second screw and of a third screw, the holes being formed symmetrically relative to a central U-shaped body 12 and to its channel 20, in lateral projections 13. An eye 14 is arranged on the side of the body 12 and essentially in an extension of its base 15. The axis X2 of a hole 16 of the eye 14 is oriented in such a way that, when the saddle 9 is positioned on the sacrum, the corresponding screw is inserted into the sacral plate and towards the upper axis of the latter, as in the case of the saddle 10. The axes Y2 of the holes 11 are for their part inclined by a suitable angle to a median plane of the channel 4 passing through its base 15, and the corresponding screws converge towards one another, one of them being driven into the iliac mass when the saddle 9 is positioned.

FIG. 3 shows a third embodiment, a saddle 17 comprising two eyes 18 arranged on each side of a U-shaped body 19 and essentially in an extension of the base 15 of a channel 30, but with a lateral off-set relative to the axis of the base 15. Walls 19a and 19b of the body 19 present a defined inclination to the general plane of the two eyes 18, either on one side or the other. This inclination is preferably equal, for reasons of ease of assembly, to that of the axis Y3 of a hole 21 made in the base 15 of the channel 4 and intended to receive a screw (not shown). The axes X3 have different inclinations to the general plane of the eyes 18, so that the three screws inserted into the holes 21 and 22 form a divergent assembly.

In a fourth embodiment shown in FIG. 4, a saddle 23 comprises two U-shaped bodies, of which the channels 25 are aligned and which are connected via an eye 26 in which a screw hole 27 is made. An axis X4 of the hole 27 presents an inclination similar to that of axes X3, X2, X1 in such a way that the corresponding screw can likewise be inserted into the sacral plate. A hole 28 for passage of a second screw is made in the base of one of the bodies 24, and its axis Y4 is inclined in such a way that the corresponding screw can be inserted into the iliac mass when the saddle 23 is positioned on the sacrum.

In this embodiment, as in the three preceding embodiments, tappings 6 are made on the opposite inside walls of the U-shaped bodies 24 and are intended to receive a threaded plug, such as 7, for locking the rod 8 in the bodies 24.

Figure 5:
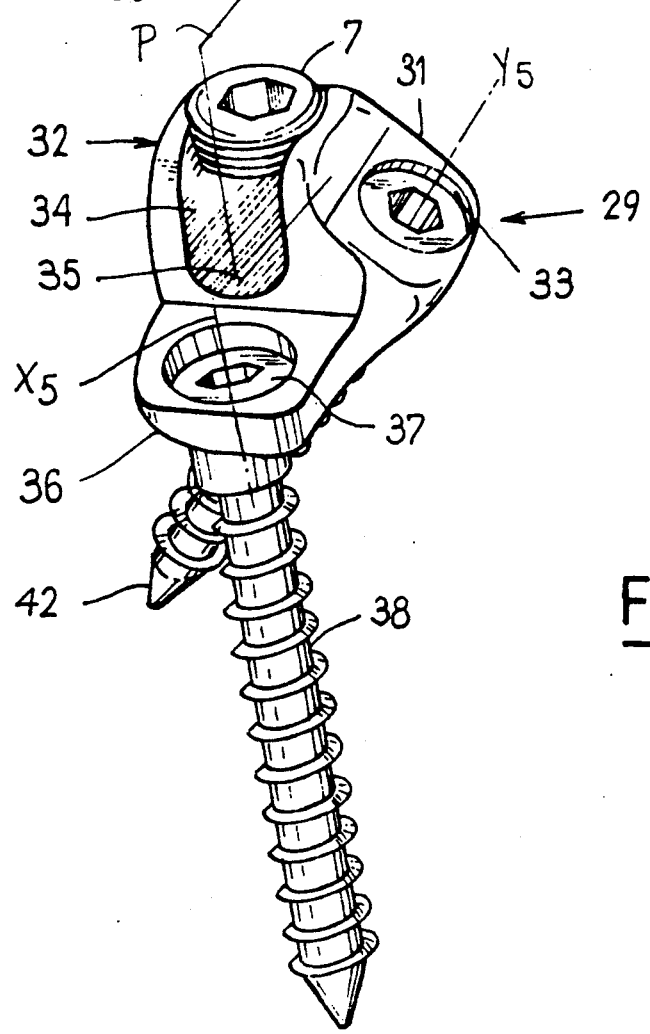
FIG. 5 is a perspective view of a fifth embodiment of the saddle according to the invention, equipped with two screws.

FIG. 5 illustrates a fifth embodiment of the invention, in which a saddle 29 comprises a projection 31 on the side of a U-shaped body 32. A hole 33 is made in the projection 31, with an axis Y5 inclined by a suitable angle to a median plane P of the channel 34 of the body 32, passing through the base 35 of the latter. This inclination of the axis Y5 to the plane P can be preferably of the order of about 20 to 30 degrees. The saddle 29 is completed by an eye 36 whose hole 37 has an axis X5 oriented in a manner similar to axes X4, X3, etc., in such a way that the corresponding screw 38 can be inserted in the sacral plate and towards the upper axis of the latter (FIG. 6). As in the previous embodiments, the walls of the body 32 are provided with tapped sections for receiving the threaded plug 7 for locking the rod 8 (FIG. 7), and the saddle 29 is one-piece.

A surface 39 of the body 32 and of the projection 31, which is intended to bear on the sacrum 41, is advantageously hemispherical so as to match the anatomy of the sacrum 41.

The hole 33 can receive a screw 42 which is inserted in the iliac mass, as can be seen in FIG. 6.

Figure 7:
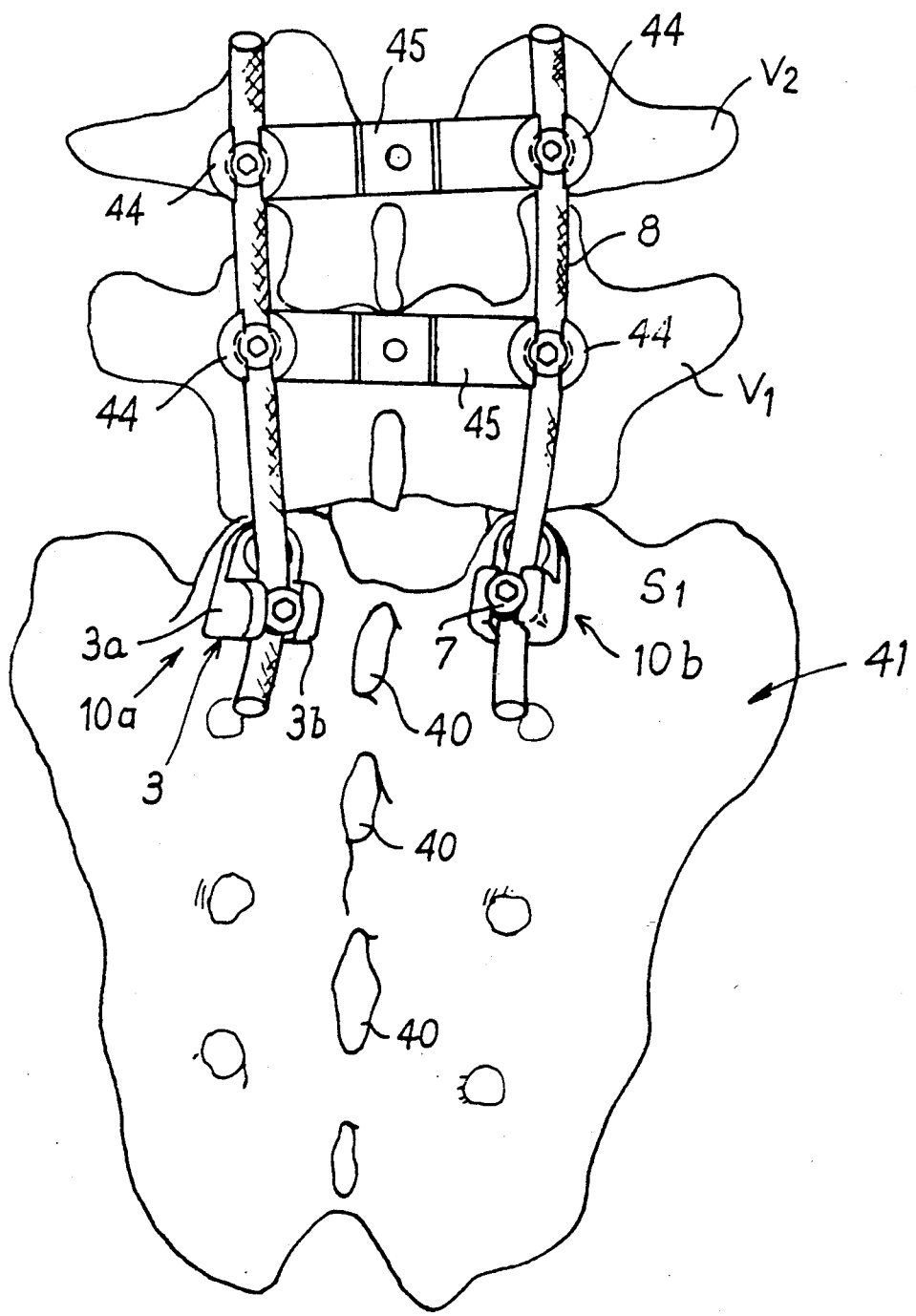
FIG. 7 is an elevation view of a spinal osteosynthesis device comprising two saddles according to FIG. 1 and positioned on the sacrum and also on the two adjacent lumbar vertebrae.

FIG. 7 shows a complete spinal osteosynthesis device with sacral support by two saddles 10 at S1 and by screws 44 on the last two lumbar vertebrae L5 and L4. The two walls 3a and 3b of the body 3 have, relative to the general plane of the eye 1, an inclination to one side or the other depending on the intended positioning of the saddle on the sacrum with respect to the line of the tubercles 40. In FIG. 7 the left-hand saddle 10a corresponds to that in FIG. 1, the walls 3a and 3b and the axis Y1 of the hole 5 having an inclination in the direction of the tubercles 40 (referred to by surgeons as an "inward" inclination). Symmetrically, the second saddle 10b arranged on the right in FIG. 7 has its walls inclined towards the tubercles 40.

A saddle such as 10 cannot therefore be used alternately to one side or the other of the tubercles 40, a set of each saddle 10a, 10b being necessary.

The same applies to the saddles 17 and 29, on account of the inclination of the walls 19a and 19b in the case of saddle 17, and on account of the lateral position of the projection 31 in the case of saddle 29. FIG. 6 in fact shows a saddle 29a identical to the saddle 29 in FIG. 5, the eye 36 being positioned in the direction of the fifth lumbar vertebra L5 and its projection 31 being positioned in the direction of the tubercles 40. In contrast, the second saddle 29b positioned to the other side of the tubercles 40 has its projection 31 positioned on the other side of the body 32 compared to the projection 31 of saddles 29 and 29a, and in the direction of the tubercles 40. For this reason the inclinations of the axes of the holes 33 and of the corresponding screws 42 are opposed, which allows them to be driven into the intended areas of the sacral wings.

It will be noted that, in contrast, saddles 9 and 23 are symmetrical relative to the median plane of their U-shaped body and can therefore be used alternately on one side or the other of the line of tubercles 40.

The positioning of a saddle according to the invention is carried out in the following manner.

The path of the first screw, such as 38, passing through the eye, is prepared. It extends from the outer part of the foot of the S1 articulation and is directed obliquely towards the line of the tubercles 40, with a slightly ascending inclination of, for example, 10 to 15 degrees. Thus, the screw 38 can be directed through the pedicle of S1 towards the upper plate of S1 in subchondral bone, so as to form a particularly firm support. The saddle is then fixed by placing this first screw 38 through the corresponding eye, such as for example 36, the U-shaped body, such as 3, having its walls inclined in the direction of the tubercles 40, as can be seen in particular in FIG. 7.

The second orifice is then prepared by placing the saddle parallel to the median line of the tubercles 40, or obliquely towards the outside by 5 to 10 degrees. The direction of the second orifice is determined by the inclination of the channel, such as 4 (FIGS. 1 and 3), of the saddle. During this preparation, the saddle is held by a suitable instrument known per se, and the second screw, such as 42, is then put into position. It is directed towards the iliac mass and must be sufficiently long to approach the cortex of the wing without passing through it. In young subjects, with a bone of good quality, this support is sufficient.

It remains for the surgeon to introduce each curved rod 8 into the open body (3, 12, etc.), and this is achieved easily without risking displacing the saddle support. Each rod 8 is then locked by means of the threaded plugs 7 being put into position.

The fixation device which can be seen in FIG. 7 comprises, in a manner known per se, the screws 44 driven into the pedicles of vertebrae L5 and L4, as well as small transverse connecting bars 45. These elements do not form part of the present invention and do not therefore require a detailed description.

The threaded plug 7 and the tappings 6 are advantageously in accordance with French Patent Application No. 88/08,538 of 24th Jun., 1988 filed by the Applicant. These locking means can be replaced by any other equivalent system without departing from the scope of the present invention.

In adolescents and young adults, the sacral support described hereinabove is generally sufficient. In contrast, in older patients, when the sacrum is porous, this support of the rod 8 must be reinforced. In this case a supplementary iliac screw is used in combination with the saddle according to the invention. The rod 8 is then fixed at the same time by the saddle and by the iliac screw. However, the use of this iliac screw does not form part of the present invention and will not therefore be described further.

Among various possible variants, it should be noted that the saddle can have a supplementary passage hole for a third screw, whose axis is divergent relative to the axis of the hole of the eye, in such a way that the corresponding third screw is oriented like the second in the iliac mass when the saddle is positioned on the sacrum. In the saddle 23 (FIG. 4) this third screw would therefore pass through a hole made in the base of the second U-shaped body 24.

I claim:

1. A sacral support saddle for a spinal osteosynthesis device, comprising:
    a saddle body having a surface for engagement with the sacrum;
    at least one U-shaped body on said saddle body defining a channel for the receipt of a rod of a spinal osteosynthesis device and having means for locking the rod in said channel of said U-shaped body;
    at least one eye on said saddle body for receiving a first screw, said at least one eye having a cylindrical hole with an axis of inclination oriented such that, when said surface of said saddle body is positioned on the sacrum in engagement therewith, the first screw is inserted into the sacral plate along said axis of inclination towards the upper axis of the sacral plate; and
    at least one further hole in said saddle body for the passage of a second screw, said further hole having an axis of inclination that is divergent relative to said axis of inclination of said cylindrical hole of said at least one eye and oriented, when said surface of said saddle body is positioned on the sacrum in engagement therewith, towards an iliac mass.

2. The saddle of said 1 wherein said U-shaped body has a base and said at least one further hole for the passage of the second screw is formed in said base.

3. The saddle of claim 1 and further comprising a second U-shaped body on said saddle body defining a channel for the receipt of the rod of the spindle osteosynthesis device aligned with said channel of the first said U-shaped body, at least one of said U-shaped bodies having said at least one further hole formed therein for the passage of the second screw, and said U-shaped bodies having said eye arranged therebetween.

4. The saddle of claim 1 wherein:
    said at least one further hole comprises two holes in said saddle body for the passage of the second screw and a third screw, said two holes being symmetrically disposed in said saddle body relative to said U-shaped body;
    said U-shaped body has a base; and
    said saddle body includes an extension extending from said base of said U-shaped body on one side of said U-shaped body, said extension having said eye therein.

5. The saddle of claim 1 wherein:
    said saddle body includes a projection on one side of said U-shaped body, said projection having said further hole therein for passage of the second screw, with said axis of inclination of said further hole being inclined relative to a medium plane of said channel of said U-shaped body by a predetermined angle;
    said U-shaped body has a base, said axis of inclination of said further hole passing through said base; and
    said saddle body further includes an extension extending from said base of said U-shaped body, said extension having said eye therein.

6. The saddle of claim 5, wherein said axis of inclination of said hole of said eye is inclined relative to the medium plane of said channel approximately 20 to 30 degrees.

7. The saddle of claim 5, wherein said surface of said saddle body is hemispherical.

8. The saddle of claim 1, wherein said at least one eye comprises two eyes disposed on either side of said U-shaped body.

9. The saddle of claim 8, wherein:
    said U-shaped body has a base; and
    said saddle body comprises one extension from one side of said base in the direction of said channel, having one said eye therein, and a second extension, extending from the other side of said base offset relative to the direction of said channel, having the second said eye therein.

10. The saddle of claim 1, wherein said means for locking comprises threaded walls in said U-shaped body and a threaded plug which can be screwed into said threaded walls.

11. The saddle of claim 1, wherein said U-shaped body comprises walls defining the U-shape and said channel, said walls being inclined relative to said axis of inclination of said hole of said eye.

12. An assembly for a spinal osteosynthesis device, comprising:
    a sacral support saddle comprising:
        a saddle body having a surface for engagement with the sacrum,
        at least one U-shaped body on said saddle body defining a channel for the receipt of a rod of a spinal osteosynthesis device and having means for locking the rod in said channel of said U-shaped body,
        at least one eye on said saddle body for receiving a screw, said at least one eye having a cylindrical hole with an axis of inclination oriented such that when said surface of said saddle body is positioned on the sacrum in engagement therewith, a screw inserted into the sacral plate will extend along said axis of inclination towards the upper axis of the sacral plate, and
        at least one further hole in said saddle body for the passage of another screw, said further hole having an axis of inclination that is divergent relative to said axis of inclination of said cylindrical hole of said at least one eye and oriented, when said surface of said saddle body is positioned on the sacrum in engagement therewith, towards an iliac mass;
    a first screw for each of said eyes; and
    a second screw for each of said further holes.

* * * * *